US00PP31986P2

(12) United States Plant Patent
Hardy

(10) Patent No.: US PP31,986 P2
(45) Date of Patent: Jul. 14, 2020

(54) ***GAILLARDIA* PLANT NAMED 'HARAPHON'**

(50) Latin Name: ***Gaillardia* x *grandiflora***
Varietal Denomination: HARAPHON

(71) Applicant: Rosemary Hardy, Hampshire (GB)

(72) Inventor: Rosemary Hardy, Hampshire (GB)

( * ) Notice: Subject to any disclaimer, the term of this patent is extended or adjusted under 35 U.S.C. 154(b) by 0 days.

(21) Appl. No.: 16/501,702

(22) Filed: May 23, 2019

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431
CPC ..... A01H 6/14
See application file for complete search history.

*Primary Examiner* — Anne Marie Grunberg
(74) *Attorney, Agent, or Firm* — Cassandra Bright

(57) ABSTRACT

A new and distinct *Gaillardia* plant named 'HARAPHON' is disclosed, characterized by unique apricot-yellow flowers. Plants are well branched, flower abundantly and typically grow to 60 cm in height. The new variety is a *Gaillardia*, normally produced as an outdoor garden or container plant.

2 Drawing Sheets

Figure 1:
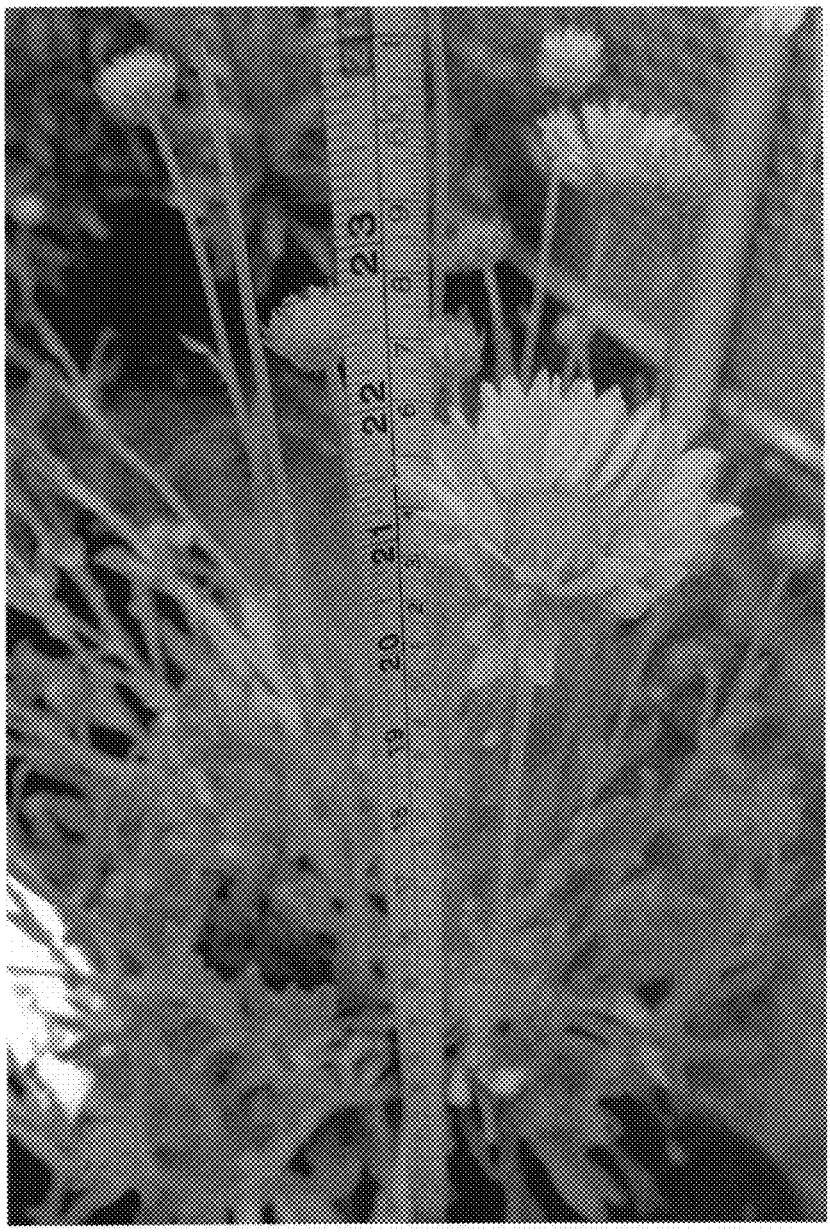

Latin name of the genus and species: *Gaillardia* x *grandiflora.*

Variety denomination: 'HARAPHON'.

BACKGROUND OF THE INVENTION

The new *Gaillardia* cultivar is a product of a planned breeding program conducted by the inventor, Rosemary Hardy, at a commercial nursery in High Hurstwood, United Kingdom. The objective of the breeding program was to produce new *Gaillardia* varieties for ornamental commercial applications. The open pollination resulting in this new variety was made during late Summer of 2013.

The seed parent is the unpatented, variety *Gaillardia grandiflora* 'Naomi Sunshine'. The pollen parent is unknown, as the crossing resulting in 'HARAPHON' was an open pollination, with unidentifiable pollen parents. The new variety was selected in June 2014 by the inventor in a group of seedlings resulting from the 2014 open-pollination in High Hurstwood, United Kingdom.

Asexual reproduction of the new cultivar 'HARAPHON' by terminal vegetative cuttings was first performed at a greenhouse in High Hurstwood, United Kingdom during the Summer of 2014 and has shown that the unique features of this cultivar are stable and reproduced true to type in successive generations. First sale of plants of this new variety occurred May 26, 2018 in the United Kingdom. This access came directly or indirectly from the inventor, qualifying for the exception allowed under 102(b). Previous to this sale, although the variety may have been publicized in print, plants were not available to the public for propagation.

SUMMARY OF THE INVENTION

The cultivar 'HARAPHON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HARAPHON' These characteristics in combination distinguish 'HARAPHON' as a new and distinct *Gaillardia* cultivar:

1. Unique apricot-yellow flowers.
2. Abundant flowering.
3. Plant height averaging 60 cm.
4. Abundant branching.

PARENT COMPARISON

Plants of the new cultivar 'HARAPHON' are similar to plants of the seed parent, in most horticultural characteristics, however, plants of the new cultivar 'HARAPHON' differ in the following:

1. The new variety produces flowers of a softer shade of apricot-yellow than the seed parent.
2. Plants of 'HARAPHON' are taller than plants of the seed parent by 10 cm on average.

COMMERCIAL COMPARISON

Plants of the new cultivar 'HARAPHON' are comparable to the variety *Gaillardia* 'Oranges and Lemons', U.S. Plant Pat. No. 17,092. The two *Gaillardia* varieties are similar in most horticultural characteristics, however, the new variety 'HARAPHON' differs in the following:

1. Plants of 'HARAPHON' are on average 60 cm tall, whereas plants of 'Oranges and Lemons' are 70 to 80 cm tall under the same conditions.
2. Plants of 'HARAPHON' are on average 45 cm wide whereas plants of 'Oranges and Lemons' are 60 cm wide under the same conditions.
3. Flower color of 'HARAPHON' is a softer apricot-yellow, compared to the stronger orange-yellow flower color of 'Oranges and Lemons'.

BRIEF DESCRIPTION OF THE PHOTOGRAPHS

The accompanying photograph in FIG. 1 illustrates in full color a typical plant of 'HARAPHON' grown in a nursery in a 2 liter pot. Age of the plant photographed is approximately 8 months from a rooted cutting.

Figure 2:
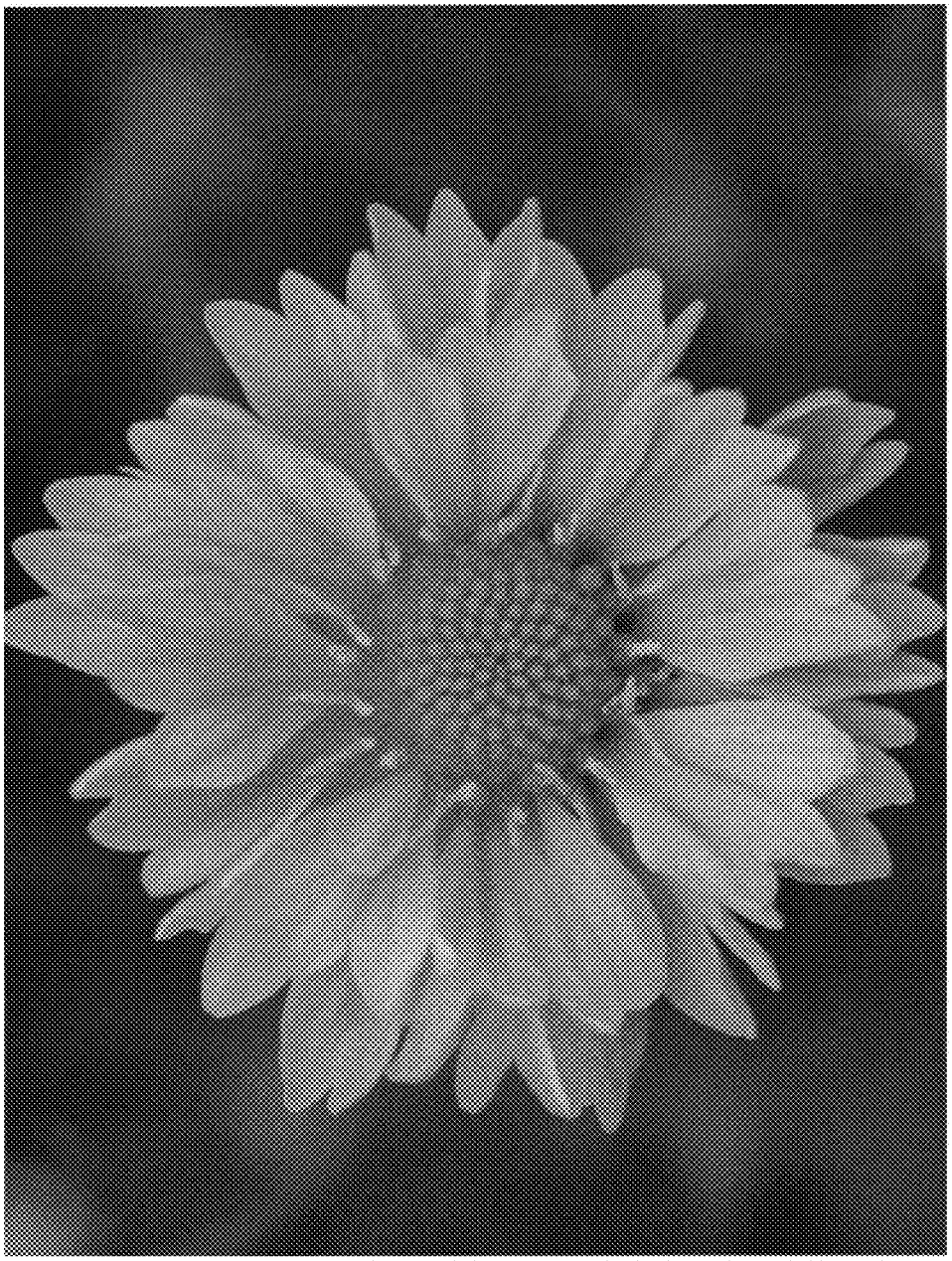

FIG. 2 illustrates in full color a close up of a typical bloom of 'HARAPHON'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'HARAPHON' plants grown outdoors during Spring in High Hurstwood, United Kingdom. The growing temperature ranged from 8° C. to 25° C. during the day and from 3° C. to 12° C. during the night. General light conditions are bright, normal sunlight. Measurements and numerical values represent averages of typical plant types. Plants are approximately 120 days old from a rooted cutting.

Botanical classification: *Gaillardia* x *grandiflora* 'HARAPHON'.

PROPAGATION

Time to initiate roots: 5 to 10 days at 20° C.

Root description: Fleshy, fine, well-branched.

PLANT

Growth habit: Compact, well branched, open.

Pot size of plant described: 16 cm.

Height: 60 cm.

Plant spread: 45 cm.

Growth rate: Moderate, becoming faster as day length increases.

Branching characteristics: Prolific, up to six branches produced without pinching. Each branch produces a single terminal inflorescence. Each branch produces further sub-branches from the lower nodes. All sub-branches produce a single terminal inflorescence.

Branching angle: Approximately 30°.

Length of primary lateral branches: 25 to 30 cm.

Quantity of primary lateral branches: 5 or more.

Characteristics of primary lateral branches:

- *Diameter.*—0.25 to 0.35 cm.
- *Color.*—RHS Yellow-Green 144A.
- *Texture.*—Lightly covered with thin soft hairs.
- *Strength.*—Very strong.

Internodes length: 3 to 3.5 cm.

FOLIAGE

Leaf:

- *Shape.*—Oblong.
- *Quantity.*—Approximately 35 per branch.
- *Average Length.*—10 cm.
- *Average Width.*—1.8 to 2.4 cm.
- *Apex.*—Acute.
- *Base.*—Acuminate to cuneate.
- *Margin.*—Entire.
- *Texture.*—Rough.
- *Pubescence.*—Scabrous.
- *Aspect.*—20 to 25° upwards.
- *Color.*—Young foliage upper side: RHS Green 137D. Young foliage under side: RHS Green 137D. Mature foliage upper side: RHS Green 137C. Mature foliage under side: RHS Yellow-Green 147B.
- *Venation.*—Type: Pinnate. Venation color upper side: RHS Yellow-Green 146C. Venation color under side: RHS Yellow-Green 146D.
- *Petiole.*—Absent.

FLOWER

Natural flowering season: Late March to November.

Days to flowering from rooted cutting: 4 to 6 weeks.

Inflorescence and flower type and habit: Terminal occurring composite.

Rate of flower opening: 3 to 5 days from bud to fully opened flower.

Flower longevity on plant: 5 to 7 days.

Persistent or self-cleaning: Self-cleaning.

Flower size:

- *Diameter of entire flower.*—Approximately 7 cm.
- *Depth of flower.*—Approximately 3 cm.
- *Disc diameter.*—Approximately 2 cm.
- *Quantity of inflorescences per lateral stem.*—6 to 7.
- *Quantity of open inflorescences and buds per plant.*—35 to 50.

Bud:

- *Shape.*—Flattened globular.
- *Length.*—1 cm.
- *Diameter.*—1.6 cm.
- *Color.*—Ray florets: RHS Yellow-Green 150C. Disc florets: Between RHS Yellow-Green 144B and 144C.

Ray florets:

- *Quantity.*—Average 13.
- *Arrangement.*—Rotate in a single whorl.
- *Length.*—2.7 cm.
- *Width.*—3.4 cm.
- *Shape.*—4-lobed.
- *Apex.*—Obtuse.
- *Base.*—Attenuate.
- *Margin.*—Entire.
- *Texture, upper and lower surfaces.*—Smooth; slightly ribbed lengthwise.
- *Color.*—When opening: Upper Surface: RHS Yellow 13A. Lower Surface: RHS Yellow 12B. Fully opened: Upper Surface: RHS Yellow-Orange 21B and 21C at tip, between Orange 28C and 28D at base. Lower Surface: between RHS Yellow 13A and 14A at tip, blushed Orange 24B near base.

Disc florets:

- *Quantity.*—Approximately 135.
- *Arrangement.*—Spirally placed on disc.
- *Length.*—1 cm.
- *Width.*—0.2 cm.
- *Shape.*—Tubular.
- *Apex.*—Emarginated.
- *Base.*—Fused.
- *Margin.*—Entire.
- *Texture, all surfaces.*—Covered with short, soft hairs, resulting in velvet texture.
- *Color.*—Young: RHS Yellow-Orange near base, between RHS Yellow-Green 150B and 150D at tips. Mature: RHS Yellow-Orange 17A near base, 14B at tips.

Phyllaries/involucral bracts:
*Quantity*.—Approximately 29.
*Length*.—1.0 to 1.9 cm (three spiral rows of involucral bracts, the row near petals are shorter than those that are far from petals, range given).
*Width*.—0.2 to 0.7 cm (three spiral rows of involucral bracts, the row near petals are narrower than those that are far from the petals, range given).
*Shape* (*overall*).—Lanceolate.
*Apex*.—Acute.
*Base*.—Cuneate.
*Texture*.—Dull, covered with short thin hairs.
*Margin*.—Entire, with short hair directly on margin.
*Color*.—Between RHS Green 137D and 138A.
Peduncles:
*Length*.—Average 15 to 20 cm.
*Diameter*.—0.3 cm.
*Angle*.—About 45° to the lateral branch.
*Strength*.—High.
*Texture*.—Slightly glossy due to short and delicate hairs.
*Color*.—RHS Yellow-Green 145B.
Fragrance: Slightly sweet scent.

REPRODUCTIVE ORGANS

Ray florets: No reproductive organs observed.
Disc florets:
Stamens:
*Number*.—5.
Anthers:
*Shape*.—Obovate.
*Length*.—Approximately 0.5 mm.
*Color*.—RHS Yellow 10A.
*Pollen*.—Color: RHS Yellow-Orange 21 A. Quantity: Abundant.
Pistil:
*Number*.—1.
*Length*.—1.4 mm.
*Style*.—Length: 5 mm. Color: RHS Yellow 2C.
*Stigma*.—Shape: Bifid. Color: RHS Yellow 2D. Ovary Color: RHS Yellow 1D.

OTHER CHARACTERISTICS

Seeds and fruits: More than 30 seeds per flower.
*Shape*.—Oblong triangle base, color RHS 197D.
*Length*.—0.2 cm.
*Width*.—0.15 cm.
*With spiny crown on top*.—Length: 0.3 cm. Width: 0.2 cm. Crown color: RHS 192D.
Disease/pest resistance: Neither resistance nor susceptibility to normal diseases and pests of *Gaillardia* x *grandiflora* have been observed.
Temperature tolerance: Expected tolerance USDA Zones 3-10. Typical for species.

What is claimed is:

1. A new and distinct cultivar of *Gaillardia* plant named 'HARAPHON' as herein illustrated and described.

* * * * *